(12) United States Patent
Chenchik et al.

(10) Patent No.: US 6,352,829 B1
(45) Date of Patent: *Mar. 5, 2002

(54) METHODS OF ASSAYING DIFFERENTIAL EXPRESSION

(75) Inventors: Alex Chenchik, Palo Alto; George Jokhadze, Mountain View, both of CA (US); Robert Bibilashvilli, Moscow (RU)

(73) Assignee: Clontech Laboratories, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/225,928

(22) Filed: Jan. 5, 1999

Related U.S. Application Data

(63) Continuation-in-part of application No. 08/859,998, filed on May 21, 1997, now Pat. No. 5,994,076.

(51) Int. Cl.[7] .......................... C12Q 1/68; C12P 19/34; C07H 21/02; C07H 21/04
(52) U.S. Cl. .......................... 435/6; 435/91.1; 435/91.2; 536/23.1; 536/24.3; 536/24.31; 536/24.33
(58) Field of Search .......................... 435/6, 91.2, 91.1, 435/24.3; 536/24.31, 24.33, 23.1

(56) References Cited

PUBLICATIONS

Ehlers et al. J. Exp. Med. 173:25–36. Jan. 1991.*
Chalifour et al. Analytical Biochem. 216:299–304, (1991).*
Wei et ala. Cancer Research (Nov. 1, 1995) 55(21) 5025–9.*

* cited by examiner

*Primary Examiner*—Jeffrey Fredman
*Assistant Examiner*—Juliet C. Einsmann
(74) *Attorney, Agent, or Firm*—Bret E. Field; Bozicevic, Field & Francis

(57) ABSTRACT

Methods and compositions are provided for analyzing differences in the RNA profiles between a plurality of different physiological samples. In the subject methods, a set of a representational number of distinct gene specific primers is used to generate labeled nucleic acids from each of the different physiological samples. The labeled nucleic acids are then compared to each other and differences in the RNA profiles are determined. The subject methods find use in methods of identifying differential gene expression.

10 Claims, No Drawings

METHODS OF ASSAYING DIFFERENTIAL EXPRESSION

CROSS-REFERENCE TO RELATED APPLICATIONS

This application is a continuation-in-part of application Ser. No. 08/859,998, now U.S. Pat. No. 5,994,076 filed May 21, 1997, the disclosure of which is herein incorporated by reference.

INTRODUCTION

1. Technical Field

The technical field of this invention is the analysis of differential gene expression.

2. Background

In higher organisms, any given cell expresses only a fraction of the total number of genes present in its genome. The small fraction of the total number of genes that is expressed determine the life processes carried out by the cell, e.g. development and differentiation, homeostasis, response to insults, cell cycle regulation, aging, apoptosis, and the like. Alterations in gene expression decide the course of normal cell development and the appearance of diseased states, such as cancer. Because the choice of which genes are expressed has such a profound effect on the nature of any given cell, methods of analyzing gene expression are of critical import to basic molecular biological research. Identification of differentially-expressed genes can provide a key to diagnosis, prognosis and treatment of a variety of diseases or condition states in animals, including humans, and plants. Additionally, these methods can be used to identify differentially-expressed sequences due to changes in gene expression level associated with predisposition to disease, influence of external treatments, factors or infectious agents. Identification of such genes helps in development of new drugs and diagnostic methods for treating or preventing the occurrence of such diseases.

One way of analyzing gene expression in a particular cell is to perform differential gene expression assays, in which the expression of genes in different cells is compared and any discrepancies in expression are identified, where the presence of discrepancies indicates a difference in the classes of genes expressed in the cells being compared.

One method currently employed to identify differentially expressed genes begins with the generation of cDNA "targets" obtained from analogous cells, tissues or organs of a healthy and diseased organism. The cDNA targets are then hybridized to a set of target nucleic acid "probe" fragments immobilized on membrane. Differences between he resultant hybridization patterns are then detected and related to differences in gene expression in the two sources. In this procedure the number of analyzed gene-specific probes can reach several hundred thousand.

Modifications have been made to the above basic method in order to obtain improved results. These modifications include replacement of the traditional radioactive labeling procedure of the target nucleic acid sequences with nonisotopic labels, mainly fluorescent labels. Other modifications have focused on improved methods of immobilization of an array of the probe nucleic acids to surfaces of a variety of solid supports.

Despite the promise of analysis of differential expression using arrays of probes on solid supports, there is a continuing need for improvement of the methods currently employed by researchers. In current methods, hybridization of "target" to "probe" is slow. Furthermore, a number of additional events such as competitive hybridization events between distinct target sequences, nonspecific binding between "target" and "probe," and formation of secondary structures in target sequences can occur which adversely effect the results.

Accordingly, there is continued interest in the development of new methods of analyzing differential gene expression, where such methods provide for fast hybridization and high specificity of binding of "targets" to "probes."

Relevant Literature

Patents of interest include: EP 0 328 829 B1 and U.S. Pat. Nos. 5,468,613; 5,580,726; 5,599,672; 5,512,462; 5,162,209 and 5,162,209. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299–304; Nguyen et al., Genomics (1995) 29: 207–216; Pietu et al., Genome Res. (1996) 6: 492–503; and Zhao et al., Gene (1995) 166: 207–213.

Use of non-isotopic labels in methods of differential gene expression analysis arc described in: Schena et al. Science (1995) 270: 467–470; Schena et al., Proc. Natl. Acad. Sci. USA (1996) 93: 10614–10619; DeRisi et al., Nature Genet. (1996) 14: 457–460; and Lockhart et al., Nature Biotechnol. (1996) 14: 1675–1680.

Methods of stably associating probes to the surface of substrates are described in: Hermanson, et al. Immobilized Affinity Ligand Techniques, Academic Press, (1992); WO 89/11548; European Patent No. 0 281 390 B1; WO 88/01302; European Patent Application No. 0392546; U.S. Pat. No. 5,436,327; U.S. Pat. No. 5,445,934.

Methods of improving hybridization of target to substrate surface associated probe are described in: EP 0 318 245 B1 (solution hybridization of probe to target followed by binding of hybridization complex to surface of substrate); Lockhart et al., Nature Biotechnol. (1996) 14: 1675–1680, EP 0 328 829 B1 (preamplification of target DNA/RNA); Maniatis et al., Molecular Cloning, A Laboratory Manual (Cold Spring Harbor Press, Cold Spring Harbor, N.Y., (1989), Nucleic Acid Hybridization, A Practical Approach (Hames, B. D., and Higgins, S. J. eds. IRL Press, Oxford) (1985), EP 0 229 442 (addition of an inert polymers such as dextran sulfate); U.S. Pat. No. 5,387,510, EP 0 318 245 B1 (use of "helper" oligonucleotides which reorder secondary and tertiary structure of target polynucleotide); WO 89/11548 (attaching probes to surface of substrate through long spacer arms).

Methods of improving specificity of hybridization are described in: U.S. Pat. Nos. 5,449,603 & 5,547,843 (use of single stranded nucleic acid binding protein); U.S. Pat. Nos. 4,888,274 & 5,223,414, EP 0 481 065 B1 (use of RecA protein-coated nucleoprotein target molecules); Khrapko et al., FEBS Lett. (1989) 256: 118–122 and U.S. Pat. No. 5,503,980 (continuous stacking interaction between short oligonucleotides of target and probe molecules, followed by enzymatic ligation step); and U.S. Pat. No. 5,434,047 (use of non-target probe which hybridized with non-target nucleic acid).

SUMMARY OF THE INVENTION

Methods and compositions for identifying differences between the nucleic acid profiles of a plurality of biological samples are provided. In the subject methods, a set of a representational number of different gene specific primers is used to generate labeled target nucleic acids from samples of nucleic acids, usually ribonucleic acids, derived from at least two different physiological sources. The labeled target nucleic acids derived from each physiological source are then compared, preferably by hybridization to arrays of probe nucleic acids stably associated with the surface of a substrate. The subject methods find use in differential gene expression analysis.

DESCRIPTION OF THE SPECIFIC EMBODIMENTS

Methods and compositions are provided for analyzing differences in the ribonucleic acid profiles between two or more physiological sources. In the subject methods, a set of a representational number of gene specific primers is used to generate labeled target nucleic acids from the physiological sources. The labeled target nucleic acids from each of the samples are then compared, preferably by hybridizing the labeled target nucleic acids from each sample to an array of probe nucleic acids stably associated with the surface of a substrate. Also provided are sets of gene specific primers employed in the subject methods, as well as kits comprising the sets of gene specific primers. The subject methods find use in a variety of applications, including differential gene expression assays.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Critical to the subject invention is the use of a set (i.e. pool, mixture, collection) of a representational number of gene specific primers to generate labeled nucleic acids from a sample of nucleic acids, usually ribonucleic acids (RNAs), where the labeled nucleic acids may act as "target" in subsequent hybridization assays, described in greater detail below. As used herein, the term nucleic acid is used in the broadest sense to refer to any sized multimer of nucleotide monomeric units, including short multimers such as dimers, trimers and the like, as well as longer multimers such as oligonucleotides and polynucleotides, where oligonucleotides generally denotes single stranded nucleotide multimers of from about 10 to 100 nucleotides and up to 200 nucleotides in length, and polynucleotides typically refers to single or double stranded nucleotide monomers of generally greater than 100 nucleotides in length.

As the subject sets comprise a representational number of primers, the total number of different primers in any given set will be only a fraction of the total number of different or distinct RNAs in the sample, where the total number of primers in the set will generally not exceed 80%, usually will not exceed 50% and more usually will not exceed 20% of the total number of distinct RNAs, usually the total number of distinct messenger RNAs (mRNAs), in the sample. Any two given RNAs in a sample will be considered distinct or different if they comprise a stretch of at least 100 nucleotides in length in which the sequence similarity is less then 98%, as determined using the FASTA program (default settings). As the sets of gene specific primers comprise only a representational number of primers, with physiological sources comprising from 5,000 to 50,000 distinct RNAs, the number of different gene specific primers in the set of gene specific primers will typically range from about 20 to 10,000, usually from 50 to 2,000 and more usually from 75 to 1500.

Each of the gene specific primers of the sets described above will be of sufficient length to specifically hybridize to a distinct nucleic acid member of the sample, e.g. RNA or cDNA, where the length of the gene specific primers will usually be at least 8 nt, more usually at least 20 nt and may be as long as 25 nt or longer, but will usually not exceed 50 nt. The gene specific primers will be sufficiently specific to hybridize to complementary template sequence during the generation of labeled nucleic acids under conditions sufficient for first strand cDNA synthesis, which conditions are known by those of skill in the art. The number of mismatches between the gene specific primer sequences and their complementary template sequences to which they hybridize during the generation of labeled nucleic acids in the subject methods will generally not exceed 20%, usually will not exceed 10% and more usually will not exceed 5%, as determined by FASTA (default settings).

Generally, the sets of gene specific primers will comprise primers that correspond to at least 20, usually at least 50 and more usually at least 75 distinct genes as represented by distinct mRNAs in the sample, where the term "distinct" when used to describe genes is as defined above, where any two genes are considered distinct if they comprise a stretch of at least 100 nt in their RNA coding regions in which the sequence similarity does not exceed 98%, as determined by FASTA (default settings).

The gene specific oligonucleotide primers may be synthesized by conventional oligonucleotide chemistry methods, where the nucleotide units may be: (a) solely nucleotides comprising the heterocyclic nitrogenous bases found in naturally occurring DNA and RNA, e.g. adenine, cytosine, guanine, thymine and uracil; (b) solely nucleotide analogs which are capable of base pairing under hybridization conditions in the course of DNA synthesis such that they function as the above nucleotides found in naturally occurring DNA and RNA, where illustrative nucleotide analogs include inosine, xanthine, hypoxanthine, 1,2-diaminopurine and the like; or (c) from combinations of the nucleotides of (a) and nucleotide analogs of (b), where with primers comprising a combination of nucleotides and analogues thereof, the number of nucleotide analogues in the primers will typically be less than 25 and more typically less than 5. The gene specific primers may comprise reporter or hapten groups, usually 1 to 2, which serve to improve hybridization properties and simplify detection procedure.

Depending on the particular point at which the gene specific primers are employed in the generation of the labeled nucleic acids, e.g. during first strand cDNA synthesis or following one or more distinct amplification steps, each gene specific primer may correspond to a particular RNA by being complementary or similar, where similar usually means identical, to the particular RNA. For example, where the gene specific primers are employed in the synthesis of first strand cDNA, the gene specific primers will be complementary to regions of the RNAs to which they correspond.

Each gene specific primer can be complementary to a sequence of nucleotides which is unique in the population of nucleic acids, e.g. mRNAs, with which the primers are contacted, or one or more of the gene specific primers in the set may be complementary to several nucleic acids in a given population, e.g. multiple mRNAs, such that the gene specific primer generates labeled nucleic acid when one or more of a set of related nucleic acid species, e.g. species having a conserved region to which the primer corresponds, are present in the sample. Examples of such related nucleic acid species include those comprising: repetitive sequences, such as Alu repeats, Al repeats and the like; homologous sequences in related members of a gene-family; polyadenylation signals; splicing signals; or arbitrary but conversed sequences.

The gene specific primers of the sets of primers according to the subject invention are typically chosen according to a number of different criteria. In some embodiments of the invention, primers of interest for inclusion in the set include primers corresponding to genes which are typically differentially expressed in different cell types, in disease states, in response to the influence of external agents, factors or infectious agents, and the like. In other embodiments, primers of interest are primers corresponding to genes which are expected to be, or already identified as being, differentially expressed in different cell, tissue or organism types. Preferably, at least 2 different gene functional classes will be represented in the sets of gene specific primers, where the number of different functional classes of genes represented in the primer sets will generally be at least 3, and will usually be at least 5. In other words, the sets of gene specific primers comprise nucleotide sequences complementary to RNA transcripts of at least 2 gene functional classes, usually at least 3 gene functional classes, and more usually at least 5 gene functional classes. Gene functional classes of interest include oncogenes; genes encoding tumor suppressors; genes encoding cell cycle regulators; stress response genes; genes encoding ion channel proteins; genes encoding transport proteins; genes encoding intracellular signal transduction modulator and effector factors; apoptosis related genes; DNA synthesis/recombination/repair genes; genes encoding transcription factors; genes encoding DNA-binding proteins; genes encoding receptors, including receptors for growth factors, chemokines, interleukins, interferons, hormones, neurotransmitters, cell surface antigens, cell adhesion molecules etc.; genes encoding cell-cell communication proteins, such as growth factors, cytokines, chemokines, interleukins, interferons, hormones etc.; and the like. Less preferred are gene specific primers that are subject to formation of strong secondary structures with less than −10 kcal/mol; comprise stretches of homopolymeric regions, usually more than 5 identical nucleotides; comprise more than 3 repetitive sequences; have high, e.g. more than 80%, or low, e.g. less than 30%, GC content etc.

The particular genes represented in the set of gene specific primers will necessarily depend on the nature of physiological source from which the RNAs to be analyzed are derived. For analysis of RNA profiles of eukaryotic physiological sources, the genes to which the gene specific primers correspond will usually be Class 11 genes which are transcribed into RNAs having 5' caps, e.g. 7-methyl guanosine or 2,2,7-trimethylguanosine, where Class II genes of particular interest are those transcribed into cytoplasmic mRNA comprising a 7-methyl guanosine 5' cap and a polyA tail.

For analysis of RNA profiles of mammalian physiological sources, of particular interest are gene specific primers corresponding to the functional gene classes listed above. For analysis of RNA profiles of human physiological sources, the gene specific primers of particular interest are the gene specific primers identified in Table 1 of application Ser. No. 08/859,008, now U.S. Pat. No. 5,961,834 filed May 21, 1997 (the disclosure of which is herein incorporated by reference) as SEQ ID NO:01 to SEQ ID NO:1372, where sets of these primers will usually include at least 20 and more usually at least 50 of these specific sequences. Also of interest are those gene specific primers corresponding to those genes (and specific capable of producing target capable of hybridizing to those specific regions of the genes) as listed in the following copending patent applications, the disclosures of which are herein incorporated by reference: U.S. application Ser. No. 09/221,480 entitled Apoptosis Array, now abandoned; U.S. application Ser. No. 09/222,432 entitled Cancer Array now abandoned; U.S. application Ser. No. 09/222,436 entitled Cell Cycle Array now abandoned; U.S. application Ser. No.09/222,437 entitled Cell Interaction Array now abandoned; U.S. application Ser. No. 09/222,251 entitled Cytokine Receptor Array now abandoned; U.S. application Ser. No. 09/221,481 entitled Human Array; U.S. application Ser. No. 09/222,256 entitled Human Stress Array; U.S. application Ser. No. 09/222,248 entitled Mouse Array now U.S. Pat. No. 6,077,673; and U.S. application Ser. No. 09/222,253 entitled Oncogene/Tumor Suppressor Array now abandoned.

Depending on the particular nature of the labeled nucleic acid generation step of the subject methods, the gene specific primers may be modified in a variety of ways. One way the gene specific primers may be modified is to include an anchor sequence of nucleotides, where the anchor is usually located 5' of the gene specific portion of the primer and ranges in length from 10 to 50 nt in length, usually 15 to 40 nt in length. The anchor sequence may comprise a sequence of bases which serves a variety of functions, such as a sequence of bases which correspond to the sequence found in promoters for bacteriophage RNA polymerase, e.g. T7 polymerase, T3 polymerase, SP6 polymerase, and the like; arbitrary sequences which can serve as subsequent primer binding sites; and the like.

Turning now to the methods employing the above sets of gene specific primers, the first step in the subject methods is to obtain a sample of nucleic acids, usually RNAs or nucleic acid derivatives thereof, from a physiological source, usually a plurality of physiological sources, where the term plurality is used to refer to 2 or more distinct physiological sources. The physiological source of RNAs will typically be eukaryotic, with physiological sources of interest including sources derived single celled organisms such as yeast and multicellular organisms, including plants and animals, particularly mammals, where the physiological sources from multicellular organisms may be derived from particular organs or tissues of the multicellular organism, or from isolated cells derived therefrom. Thus, the physiological sources may be different cells from different organisms of the same species, e.g. cells derived from different humans, or cells derived from the same human (or identical twins) such that the cells share a common genome, where such cells will usually be from different tissue types, including normal and diseased tissue types, e.g. neoplastic, cell types. In obtaining the sample of RNAs to be analyzed from the physiological source from which it is derived, the physiological source may be subjected to a number of different processing steps, where such processing steps might include tissue homogenation, nucleic acid extraction and the like, where such processing steps are known to the those of skill in the art. Methods of isolating RNA from cells, tissues, organs or whole organisms are known to those of skill in the art and are described in Maniatis et al., Molecular Cloning: A Laboratory Manual (Cold Spring Harbor Press)(1989).

The next step in the subject methods is the generation of labeled nucleic acids representative of the nucleic acid, usually RNA, profile of the physiological source. As mentioned above, a set or pool of gene specific primers is used to generate the labeled nucleic acids from the sample of RNAs, where the labeled nucleic acids generated in this step may serve as "target" in subsequent assays in which the differences in the RNA profiles of at least two sources are analyzed. Since the subject sets or pools of primers are employed, a sub-population of nucleic acids is generated from the initial source, where the sub-population corresponds to only a portion or fraction of the initial nucleic acid source. As used herein, the term "target" refers to single stranded RNA, single stranded DNA and double stranded DNA, where the target is generally greater than 50 nt in length.

The set of primers may be used either in first strand cDNA synthesis or following one or more amplification steps. Furthermore, the actual synthesis of the labeled nucleic acids may be at the same step during which the sets of gene specific primers are employed, or the synthesis of the labeled nucleic acids may be one more steps subsequent to the step in which the sets of gene specific primers are employed.

In a first embodiment of the invention, the set of gene specific primers is used to generate labeled first strand cDNA, where the labeled first strand cDNA is representative of the RNA profile of the physiological source being assayed. The labeled first strand cDNA is prepared by contacting the RNA sample with the primer set and requisite reagents under conditions sufficient for hybrid duplexes (i.e. double stranded primer complexes) to be produced followed by reverse transcription of the RNA template in the sample. Requisite reagents contacted with the primers and RNAs are known to those of skill in the art and will generally include at least an enzyme having reverse transcriptase activity and dNTPs in an appropriate buffer medium.

A variety of enzymes, usually DNA polymerases, possessing reverse transcriptase activity can be used for the first strand cDNA synthesis step. Examples of suitable DNA polymerases include the DNA polymerases derived from organisms selected from the group consisting of a thermophilic bacteria and archaebacteria, retroviruses, yeasts, Neurosporas, Drosophilas, primates and rodents. Preferably, the DNA polymerase will be selected from the group consisting of Moloney murine leukemia virus (M-MLV) as described in U.S. Pat. No. 4,943,531 and M-MLV reverse transciptase lacking RNaseH activity as described in U.S. Pat. No. 5,405,776 (the disclosures of which patents are herein incorporated by reference), human T-cell leukemia virus type I (HTLV-I), bovine leukemia virus (BLV), Rous sarcoma virus (RSV), human immunodeficiency virus (HIV) and Thermus aquaticus (Taq) or Thermus thermophilus (Tth) as described in U.S. Pat. No. 5,322,770, the disclosure of which is herein incorporated by reference. Suitable DNA polymerases possessing reverse transcriptase activity may be isolated from an organism, obtained commercially or obtained from cells which express high levels of cloned genes encoding the polymerases by methods known to those of skill in the art, where the particular manner of obtaining the polymerase will be chosen based primarily on factors such as convenience, cost, availability and the like.

The various dNTPs and buffer medium necessary for first strand cDNA synthesis through reverse transcription of the primed RNAs may be purchased commercially from various sources, where such sources include Clontech, Sigma, Life Technologies, Amersham, Boehringer-Mannheim. Buffer mediums suitable for first strand synthesis will usually comprise buffering agents, usually in a concentration ranging from 10 to 100 $\mu$M which typically support a pH in the range 6 to 9, such as Tris-HCl, HEPES-KOH, etc.; salts containing monovalent ions, such as KCl, NaCl, etc., at concentrations ranging from 0–200 mM; salts containing divalent cations like $MgCl_2$, Mg(OAc) etc, at concentrations usually ranging from 1 to 10 mM; and additional reagents such as reducing agents, e.g. DDT, detergents, albumin and the like. The conditions of the reagent mixture will be selected to promote efficient first strand synthesis. Typically the set of primers will first be combined with the RNA sample at an elevated temperature, usually ranging from 50 to 95° C., followed by a reduction in temperature to a range between about 0 to 60° C., to ensure specific annealing of the primers to their corresponding RNAs in the sample. Following this annealing step, the primed RNAs are then combined with dNTPs and reverse transcriptase under conditions sufficient to promote reverse transcription and first strand cDNA synthesis of the primed RNAs. By using appropriate types of reagents, all of the reagents can be combined at once if the activity of the polymerase can be postponed or timed to start after annealing of the primer to the RNA.

In this embodiment, one of either the gene specific primers or dNTPs, preferably the dNTPs, will be labeled such that the synthesized cDNAs are labeled. By labeled is meant that the entities comprise a member of a signal producing system and are thus detectable, either directly or through combined action with one or more additional members of a signal producing system. Examples of directly detectable labels include isotopic and fluorescent moieties incorporated into, usually covalently bonded to, a nucleotide monomeric unit, e.g. dNTP or monomeric unit of the primer. Isotopic moieties or labels of interest include $^{32}P$, $^{33}P$, $^{35}S$, $^{125}I$, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. For each sample of RNA, one can generate labeled oligos with the same labels. Alternatively, one can use different labels for each physiological source, which provides for additional assay configuration possibilities, as described in greater detail below.

In a variation of the above embodiment, where desired one can generate labeled RNA instead of labeled first strand cDNA. In this embodiment, first strand cDNA synthesis is carried out in the presence of unlabeled dNTPs and unlabeled gene specific primers. However, the primers are optionally modified to comprise a promotor for an RNA polymerase, such as T7 RNA polymerase, T3 RNA polymerase, SP6 RNA polymerase, and the like. In this embodiment, following first strand cDNA synthesis, the resultant single stranded cDNA is then converted to double stranded cDNA, where the resultant double stranded cDNA comprises the anchor sequence comprising the promoter region. Conversion of the mRNA:cDNA hybrid following first strand synthesis can be carried out as described in Okayama & Berg, Mol. Cell. Biol. (1982) 2:161–170, and Gubler & Hoffman, Gene (1983) 25: 253–269, where briefly the RNA is digested with a ribonuclease, such as *E.coli* RNase H, followed by repair synthesis using a DNA polymerase like DNA polymerase I, etc., and *E.coli* DNA ligase. One may also employ the modification of this basic method described in Wu, R, ed., Methods in Enzymology (1987), vol. 153 (Academic Press). Next, the double stranded cDNA is contacted with RNA polymerase and dNTPs, including labeled dNTPs, to produce linearly amplified labeled ribonucleic acids. For cDNA lacking the anchor sequence comprising a promoter region, a polymerase that does not need a promoter region but instead can initiate RNA strand synthesis randomly from cDNA, such as core fragment of *E. Coli* RNA polymerase, may be employed.

In another embodiment of the subject invention, the labeled nucleic acid generation step comprises one or more enzymatic amplification steps in which multiple DNA copies of the initial RNAs present in the sample are produced, from which multiple copies of the initial RNA or multiple copies of antisense RNA (aRNA) may be produced, using the polymerase chain reaction, as described in U.S. Pat. No. 4,683,195, the disclosure of which is herein incorporated by reference, in which repeated cycles of double stranded DNA denaturation, oligonucleotide primer annealing and DNA polymerase primer extension are performed, where the PCR conditions may be modified as described in U.S. Pat No. 5,436,149, the disclosure of which is herein incorporated by reference.

In one embodiment involving enzymatic amplification, the set of gene-specific primers are employed in the generation of the first strand cDNA, followed by amplification of the first strand cDNA to produce amplified numbers of labeled cDNA. In this embodiment, as a set of gene-specific primers is employed in the first strand synthesis step, only a representative proportion of the total RNA in the sample is amplified during the subsequent amplification steps.

Amplification of the first strand cDNA can be conveniently achieved by using a CAPswitch™ oligonucleotide as described in U.S. patent application Ser. No. 08/582,562, the disclosure of which is herein incorporated by reference. Briefly, the CAPswitch™ technology uses a unique CAPswitch™ oligonucleotide in the first strand cDNA synthesis followed by PCR amplification in the second step to generate a high yield of ds cDNA. When included in the first-strand cDNA synthesis reaction mixture, the CAPswitch™ oligonucleotide serves as a short extended template. When reverse transcriptase stops at the 5' end of the mRNA template in the course of first strand cDNA synthesis it switches templates and continues DNA synthesis to the end of the CAPswitch™ oligonucleotide. The resulting ss cDNA incorporates at the 3' end, sequence which is complimentary to complete 5' end of the mRNA and the CAPswitch™ oligonucleotide sequence.

Of particular interest as the CAPswitch™ oligonucleotide are oligonucleotides having the following formula:

5'-dN1-dN2- . . . dNm-rN1-rN2 . . . rNn-3' wherein:
dN represents a deoxyribonucleotide selected from among dAMP, dCMP, dGMP and dTMP;

m represents an integer 0 and above, preferably from 10 to 50;

rN represents a ribonucleotide selected from the group consisting of AMP, CMP, GMP and UMP, preferably GMP; and n represents an integer 0 and above, preferably from 3 to 7.

The structure of the CAPswitch™ oligonucleotide may be modified in a number of ways, such as by replacement of 1 to 10 nucleotides with nucleotide analogs, incorporation of terminator nucleotides, such as 3'-amino NMP, 3'-phosphate NMP and the like, or non-natural nucleotides which can improve efficiency of the template switching reaction but still retain the main function of the CAPswitch™ oligonucleotide i.e. CAP-depended extension of full-length cDNA by reverse transcriptase using CAPswitch™ oligonucleotide as a template.

In using the CAPswitch™ oligonucleotide, first strand cDNA synthesis is carried out in the presence of a set of gene specific primers and a CAPswitch™ oligonucleotide, where the gene specific primers have been modified to comprise an arbitrary anchor sequence at their 5' ends. The first strand cDNA is then combined with primer sequences complementary to: (a) all or a portion of the CAPswitch™ oligonucleotide and (b) the arbitrary anchor sequence of the gene specific primers and additional PCR reagents, such as dNTPs, DNA polymerase, and the like, under conditions sufficient to amplify the first strand cDNA. Conveniently, PCR is carried out in the presence of labeled dNTPs such that the resultant, amplified cDNA is labeled and serves as the labeled or target nucleic acid. Labeled nucleic acid can also be produced by carrying out PCR in the presence of labeled primers, where either or both the CAPswitch™ oligonucleotide complementary primer and anchor sequence complementary primer may be labeled. In yet an alternative embodiment, instead of producing labeled amplified cDNA, one may generate labeled RNA from the amplified ds cDNA, e.g. by using an RNA polymerase such as *E. coli* RNA polymerase, or other RNA polymerases requiring promoter sequences, where such sequences may be incorporated into the arbitrary anchor sequence.

Instead of using the set of gene specific primers in the first strand cDNA synthesis step followed by subsequent amplification of only a representative fraction of the total number of distinct RNA species in the sample, one may also amplify all of the RNAs in the sample and use the set of gene specific primers to generate labeled nucleic acid following amplification. This embodiment may find use in situations where the RNA of interest to be amplified is known or postulated to be in small amounts in the sample.

In this embodiment, first strand synthesis is carried out using: (a) an oligo dT primer that usually comprises an arbitrary anchor sequence at its 5' end and (b) a CAPswitch™ oligonucleotide. During first strand synthesis the oligo(dT) anneals to the polyA tail of the mRNA in the sample and synthesis extends beyond the 3' end of the RNA to include the CAPswitch™ oligonucleotide, yielding a first strand cDNA comprising an arbitrary sequence at its 5' end and a region complementary to the CAPswitch™ oligonucleotide at its 3' end. The length of the dT primer will typically range from 15 to 30 nts, while the arbitrary anchor sequence or portion of the primer will typically range from 15 to 25 nt in length.

Following first strand synthesis, the cDNA is amplified by combining the first strand cDNA with primers that correspond at least partially to the anchor sequence and the CAPswitch™ oligonucleotide under conditions sufficient to produce an amplified amount of the cDNA. Labeled nucleic acid is then produced by contacting the resultant amplified cDNA with a set of gene specific primers, a polymerase and dNTPs, where at least one of the gene specific primers and dNTPs are labeled.

The labeled nucleic acids produced above provide a representation of the total RNA profile of the particular source from which the labeled nucleic acids are generated. Accordingly, the labeled nucleic acids find use in comparing the characteristic RNA profiles of different physiological sources and identifying differences in the RNA profiles between different physiological source. Comparison of the RNA profiles of two or more physiological sources finds particular use in methods of identifying differential gene expression in two physiological samples, such as cells or tissues derived from the same or different individual organisms, where the tissues may represent different diseased or normal states, different organ or tissue types, etc.

The labeled nucleic acids of the plurality of physiological sources may be compared in a number of different ways. Thus, one may compare the labeled nucleic acids from each source by separately resolving the labeled nucleic acids from each source under substantially identical electrophoretic conditions to yield an electrophoretic pattern of resolved bands for each of the different populations of labeled nucleic acids. The resultant electrophoretic patterns can then be resolved to identify differences between the labeled nucleic acid populations, which differences can then be attributed to differences in the RNA profiles of the each of the physiological sources, where such differences can, in turn, be attributed to difference in gene expression. See Liang & Pardee, Science (1992) 257: 967. Conveniently, electrophoretic separation under identical electrophoretic conditions can be achieved by running the labeled nucleic acids derived from each physiological source of interest in separate, side by side lanes on a slab gel. Automated electrophoretic machines as described in U.S. Pat. Nos. 5,410,412; 5,275,710; 5,217,591; and 5,104,512, the disclosures of which are herein incorporated by references, may be employed to resolve the labeled nucleic acids. In a modification of the above, where each set of labeled nucleic acids or targets of each physiological source has been labeled with a distinct and distinguishable label, the opportunity arises to resolve the nucleic acids in the same electrophoretic medium, e.g. the same column or in the same lane of a slab, thereby ensuring that the nucleic acids are resolved under identical electrophoretic conditions.

Alternatively, one may hybridize the labeled nucleic acids to predefined arrays of probe polymeric molecules stably associated with the surface of a substrate, where the probe polymeric molecules are capable of sequence specific base pair hybridization with complementary labeled target nucleic acids. A variety of different arrays which may be used are known in the art. The polymeric or probe molecules of the arrays may be oligonucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g. hexose phosphodiester; peptide nucleic acids; and the like. The length of the probes will generally range from 10 to 1000 nts, where oligonucleotide probes usually range from 15 to 150 nts and more usually from 15 to 100 nts in length, and polynucleotide probes usually range in length from 150 to 1000 nts, where the polynucleotide probes may be single or double stranded, usually single stranded, and may be PCR fragments amplified from cDNA.

The probe molecules on the surface of the substrates will preferably correspond to known genes of the physiological source being analyzed so that positive hybridization events may be correlated to expression of a particular gene in the physiological source. Of particular interest are arrays of probes which correspond to a particular subset of the total genes expressed by a particular physiological source. For example, for analysis of human physiological sources, preferably the arrays of probes will correspond to a particular subset of all the expressed human genes, such as those genes associated with cell-cell communication, cancer related genes, etc. The arrays of probes may have sequences that are complementary to the template and/or non-template strands of the gene to which they correspond, depending on the nature of the labeled target nucleic acid to which they are to hybridize.

The substrates with which the probe molecules are stably associated may be fabricated from a variety of materials, including plastics, ceramics, metals, gels, membranes, glasses, and the like.

A variety of different methodologies have been developed for producing arrays of probes stably associated to the surface of a substrate. Representative methodologies include spotting methods, in which probes are immobilized or spotted on the surface of substrates as described in WO 95/35505 the disclosure of which is herein incorporated by reference, and methods in which the probes are synthesized or grown on the surface of the substrates, such as EP 0 373 203 B1 and U.S. Pat. No. 5,445,934, the disclosures of which are herein incorporated by reference. Arrays of probes spotted onto nylon membranes are described in Lennon & Lerach, Trends in Genetics (1991) 7:314–317; Gress et al., Mammalian Genome (1992) 3:609–619; Meier-Ewert et al., Nature (1993) 361:375–376; Nguyen et al., Genomics (1995) 29:207–216; Zhao et al., Gene (1995) 156:207–213; Takahashi et al., Gene (1995) 164:219–217; Milosavlijevic et al., Genome Research (1996) 6:132–141; Pietu et al., Genome Research (1996) 6:492–503; and Drmanac, Science (1993) 260:1649–1652. Arrays of probes spotted onto the surface of modified microscope glass slides are described in Shena et al., Science (1995) 270: 467–470 and Shalon et al., Genome Research (1996) 6: 639–645. Arrays in which the probes have been grown on the surface of a substrate are described in Lockhart et al., Nature Biotechnology (1996) 14:1675.

Of particular interest for use in the analysis of differential gene expression in human physiological sources are the arrays of subsets human cDNAs sold under the trademark Atlas™ by Clontech and described in CLONTECHniques (April, 1997) 12:4–7.

In analyzing the differences in the population of labeled nucleic acids generated from two or more physiological sources using the arrays described above, each population of labeled nucleic acids are separately contacted to identical probe arrays under conditions of hybridization, preferably under stringent hybridization conditions, such that labeled nucleic acids hybridize to their complementary probes on the substrate surface. Suitable hybridization conditions are well known to those of skill in the art and reviewed in Maniatis et al, supra and WO 95/21944.

As with the electrophoretic analysis, where all of the target sequences comprise the same label, different arrays will be employed for each physiological source (where different could include using the same array at different times). Alternatively, where the labels of the targets are different and distinguishable for each of the different physiological sources being assayed, the opportunity arises to use the same array at the same time for each of the different target populations.

In one preferred embodiment of assays using arrays, the number of gene specific primers used to generate the target will be chosen in view of the number of distinct probes present on the surface of the substrate of the array. In such instances, the number of gene specific primers in the set will not vary by more than 10 fold from the number of distinct probes, usually by not more than 5 fold and more usually by not more than 2 fold from the number of distinct probes in the array.

Following hybridization, non-hybridized labeled nucleic acid is removed from the support surface, conveniently by washing, generating a pattern of hybridized nucleic acid on the substrate surface. A variety of wash solutions are known to those of skill in the art and may be used.

The resultant hybridization patterns of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Following detection or visualization, the hybridization patterns may be compared to identify differences between the patterns. Where arrays in which each of the different probes corresponds to a known gene are employed, any discrepancies can be related to a differential expression of a particular gene in the physiological sources being compared.

The subject methods find use in, among other applications, differential gene expression assays. Thus, one may use the subject methods in the differential expression analysis of: (a) diseased and normal tissue, e.g. neoplastic and normal tissue, (b) different tissue or subtissue types; and the like.

Also provided are kits for use in carrying out the subject methods, e.g. generating populations of labeled nucleic acids, performing differential gene expression analysis and the like. The kits according to the subject invention include at least the set of gene specific primers that are employed to generate the labeled oligonucleotides. Of particular interest are kits comprising a set of primers selected from the primers identified as SEQ ID NO: 01–1372 in application Ser. No. 08/859,008 filed May 21, 1997, the disclosure of which is herein incorporated by reference, where in these kits of particular interest, at least twenty, usually at least 50 and more usually at least 100 of the gene specific primers in the kit will be selected from this group of primers identified as SEQ ID NO: 01–1372. Also of interest are kits comprising those gene specific primers corresponding to those genes (and specific capable of producing target capable of hybridizing to those specific regions of the genes) as listed in the following copending patent applications, the disclosures of which are herein incorporated by reference: U.S. application Ser. No. 09/221,480 entitled Apoptosis Array now abandoned; U.S. application Ser. No. 09/222,432 entitled Cancer Array now abandoned; U.S. application Ser. No. 09/222,437 entitled Cell Cycle Array now abandoned; U.S. application Ser. No. 09/222,437 entitled Cell Interaction Array; U.S. application now abandoned Ser. No. 09/222,251 entitled Cytokine Receptor Array now abandoned; U.S. application Ser. No. 09/221,481 entitled Human Array; U.S. application Ser. No. 09/222,256 entitled Human Stress Array; U.S. application Ser. No. 09/222,248 entitled Mouse Array now U.S. Pat. No. 6,077,673; and U.S. application Ser. No. 09/222,253 entitled Oncogene/Tumor Suppressor Array now abandoned. The kits may further comprise one or more additional reagents employed in the various methods, such as additional non-gene specific primers sequences, such as SEQ ID NO: 1373 to 1375 of application Ser. No. 08/859, 008 filed May 21, 1997, the disclosure of which is herein incorporated by reference, dNTPs and/or rNTPs, which may be either premixed or separate, one or more uniquely labeled dNTPs and/or rNTPs, such as biotinylated or Cy3 or Cy5 tagged dNTPs, enzymes, such as reverse transcriptases, DNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The following examples are offered by way of illustration and not by way of limitation. Except where noted otherwise, all percentages are by weight and all solvent mixture proportions are by volume.

EXPERIMENTAL

Example 1

Generation of $^{32}$P-labeled Oligonucleotides During First Strand cDNA Synthesis Step A. cDNA Synthesis/Labeling Procedure 1 µg of polyA+RNA was converted into $^{32}$P-labeled first-strand cDNA as follows. A sufficient volume of master mix for all labeling reactions and 1 extra reaction was prepared as follows to ensure sufficient volume. For each 10-µl labeling reaction, the following reagents were mixed:

| | |
|---|---|
| 2 µl | 5X First-strand buffer (250 µM Tris-HCl pH 8.3; 375 mM KCl; 15 mM MgCl$_2$) |
| 1 µl | 10XdNTP mix (500 µM dGTP, 500 µM dCTP, 500 µM dTTP, 5 µM dATP) |
| 4 µl | [α-$^{32}$P]dATP (Amersham, 3000 Ci/mmol, 10 mCi/ml) |
| 1 µl | MMLV reverse transcriptase (Amersham, 200 units/µl) |
| 8 µl | Final volume |

Next, the following reagents were combined in a 0.5-ml PCR test tube:

| | |
|---|---|
| 1 µg (1–2 µl) | polyA + RNA sample |
| 1 µl | 10x gene-specific primers mix (0.2 µM of each oligonucleotide ID No. 2, 4, 6, 8, 10, 12, . . ., 1372 as listed in application Serial No. 08/859,008 filed May 21, 1997, the disclosure of which is herein incorporated by reference) |

As a control, in separate test tube were mixed 1 µg of polyA+RNA sample with 1 µl of oligo dT primer (CDS1, ID No. 1373 as listed in application Ser. No. 08/859,008 filed May 21, 1997, the disclosure of which is herein incorporated by reference).

For each tube ddH$_2$O was added to a final volume of 3 ul and the contents were mixed and spun briefly in a microcentrifuge. The tubes were then incubated in a preheated PCR thermocycler at 70° C. for 2 min. The temperature in thermocycle was reduced down to 50° C. and the tube contents were incubated for 2 min. 8 µl of master mix as prepared above were added to each reaction test tube. The contents of the test tubes were then mixed by gentle pipetting. The tubes were then incubated in a PCR thermocycler for 20 min at 50° C. The reaction was then stopped by adding 1 μl of 10× termination mix (0.1 M EDTA, 1 mg/ml glycogen).

Step B. Column Chromatography

The $^{32}$P-labeled cDNAs were separated from unincorporated $^{32}$P-labeled nucleotides and small (<0.1-kb) cDNA fragments using the following procedure for each test tube. A CHROMA SPIN-200 column (CLONTECH, Palo Alto, Calif.) was placed into a 1.5-ml microcentrifuge tube, the water was allowed to drain through the column by gravity flow until the surface of the gel beads emerged in the column matrix. The sample was then applied to the center of the gel bed's flat surface and allowed to be fully absorbed into the resin bed. 25 μl of ddH$_2$O were then applied and allowed to completely drain out of the column. 200 μl of ddH$_2$O were then applied and allowed to completely drain out of the column until there was no liquid left above the resin bed. The column was then transferred to a clean 1.5-ml microcentrifuge tube.

To collect the first fraction, 100 μl of ddH$_2$O were added to the column and allowed to completely drain out of the column. The second, third and fourth fractions were collected in analogous fashion. The tubes with fractions 1–4 were then placed in scintillation counter empty vials, and Cerenkov counts for each fraction were obtained in the tritium channel. The fractions which showed the highest Cerenkov counts were pooled.

Example 2

Generation of Cy3-labeled Hybridization Polynucleotide Target from Total RNA Using Preamplification Step CAPswitch™ technology can be effectively used for construction cDNA libraries using as a template 10–100 ng of total RNA. Any conventional procedure well known in art can be used to purify this small amount of total RNA from 10–50 mg of "difficult" cells or tissues, like human biopsy tissues, pathogenic microorganisms, tissues at different developmental stages etc.

Step A. First-Strand Synthesis—Template Switching 10 pmol of cDNA synthesis primer (oligo dT primer) CDS1 (ID No. 1373): 5'-d(TCTAGAATTCAGCGGCCGC(T)30VN)-3'

(where V=G or A or C; N=G or A or T or C)
and 10 pmol of CAPswitch™ oligonucleotide (CSO1):
CSO1 (ID No. 1374): 5'-d(CTAATACGACTCACTATAGGGC)r(GGG)-3'
were annealed to 100 ng of human skeletal muscle Total RNA (CLONTECH), in a volume of 5 ml of deionized water, by heating the mixture for 2 min at 70° C., followed by cooling on ice for 2 min. First-strand cDNA synthesis was then initiated by mixing the annealed primer-RNA with 200 units of M-MLV reverse transcriptase (Amersham) in a final volume of 10 μl, containing 50 mM Tris-HCl (pH 8.3 at 22° C.), 75 mM KCl, 6 mM MgCl2, 1 mM DTT, 1 mM of each dATP, dGTP, dCTP and dTTP. The first-strand cDNA synthesis-template switching reaction was incubated at 42° C. for 1.5 hr in an air incubator and then cooled on ice.

Step B. Generation of Full-length cDNA by PCR

PCR amplification of full-length cDNA was performed using the Advantage KlenTaq Polymerase Mix (CLONTECH). Amplification was conducted in a 200-μl volume containing 2 μl of first-strand cDNA, 40 mM Tricine-KOH (pH 9.2 at 22OC), 3.5 mM Mg(OAc)$_2$, 10 mM KOAc, 75 μg/ml BSA, 200 μM of each dATP, dGTP, dCTP and dTTP, 0.2 μM of each CAPswitch™ primer (CSP1, ID No. 1375 as identified in application Ser. No. 08/859,008 filed May 21, 1997, the disclosure of which is herein incorporated by reference) and CDS1 primer and 2 μl of KlenTaq Polymerase mix. Temperature parameters of the PCR reactions were as follows: 1 min at 95° C. followed by 20–22 cycles of 95° C. for 15 sec and 68° C. for 5 min, followed by a 10-min final extension at 68° C. PCR products were examined on 1.2% agarose/EtBr gels in 1× TBE buffer. As a DNA size marker, a 1 Kb DNA ladder was used. ds cDNA was then precipitated by addition of a half volume of 4M ammonium acetate (about 35 ml) and 3.7 volumes of 95% ethanol (about 260 ml). After vortexing, the tube was immediately centrifuged at 14,000 r.p.m. in a microcentrifuge for 20 min. The pellet was washed with 80% ethanol without vortexing, centrifuged as above for 10 min, air dried, and dissolved in 10 μl of deionized water. Yield of ds cDNA after amplification step is about 5 μg.

Step C. Labeling of cDNA by Cy3-dCTP.

5 μl of ds cDNA (2.5 μg) generated after amplification step were mixed with 4 μl of a mixture of 686 antisense gene-specific primers (0.1 μM each; ID No. 2,4,6,8,10, 12, . . . 1372 as listed in application Ser. No. 08/859,008 filed May 21, 1997, the disclosure of which is herein incorporated by reference) in a 0.5-ml PCR test tube, boiled at 100° C. for 5 min and quickly cooled in the ice. To the denatured DNA/gene-specific primer mix was added 5 μl of 5× reaction buffer (250 mM Tris-HCl, pH 7.5, 50 mM MgCl$_2$, 5 mM DTT, 250 μg/ml BSA), 10 μl 2.5×dNTP mix (500 μM each of dATP, dGTP and dTTP, 350 μM dCTP and 150 μM Cy3-dCTP (Amersham)), 0.5 μl of [α-$^{32}$P]dCTP (Amersham, 3000 Ci/mmol, 10 mCi/ml) and 0.5 μl of Advantage KlenTaq mix (Clontech). The mixture was incubated at 68° C. for 10 min and the reaction stopped by adding 1 μl of 10× termination mix (0.1 M EDTA, 1 mg/ml glycogen).

Step D. Column Chromatography

To purify the Cy3-labeled cDNAs from unincorporated Cy3-labeled nucleotides and small (<0.1-kb) cDNA fragments, a CHROMA SPIN-200 column (CLONTECH) was placed into a 1.5-ml microcentrifuge tube, water was drained from the column and the sample was applied to the center of the gel bed's flat surface and allowed to be fully absorbed into the resin bed. 25 μl of ddH$_2$O were applied and allowed to completely drain out of the column. 200 μl of ddH$_2$O were applied and the buffer was allowed to completely drain out of the column until there was no liquid left above the resin bed. The column was then transferred to a clean 1.5-ml microcentrifuge tube.

To collect the first fraction, 100 μl of ddH$_2$O was added to the column and allowed to completely drain out of the column. The second, third and fourth fractions were collected in analogous fashion. The tubes with fractions 1–4 were placed in scintillation counter empty vials, and Cerenkov counts were obtained for each fraction in the tritium channel. The fractions (usually fractions 2–3) which showed the highest Cerenkov counts were pooled, and other fractions were discarded.

Example 3

Generation of cDNA Array Probe Immobilized on Nylon Membrane 686 cDNA fragments corresponding 686 different human genes were amplified from quick-clone cDNA (CLONTECH) in 686 separate test tubes using a combination of sense and antisense gene-specific primers: SEQ ID Nos. 1+2, 3+4, 5+6, 7+8, . . . 1371+1372 as listed in application Ser. No. 08/859,008 filed May 21, 1997, the disclosure of which is herein incorporated by reference. Amplification was conducted in a 100-µl volume containing 2 µl of mixture of 10 Quick-clone cDNA from placenta, brain, liver, lung, leukocytes, spleen, skeletal muscle, testis, kidney and ovary (CLONTECH), 40 mM Tricine-KOH (pH 9.2 at 22° C.), 3.5 mM Mg(OAc)$_2$, 10 mM KOAc, 75 µg/ml BSA, 200 µM of each dATP, dGTP, dCTP and dTTP, 0.2 µM of each sense and antisense gene-specific primers and 2 µl of KlenTaq Polymerase mix. Temperature parameters of the PCR reactions were as follows: 1 min at 95° C. followed by 20–35 cycles of 95° C. for 15 sec and 68° C. for 2 min; followed by a 10-min final extension at 68° C. PCR products were examined on 1.2% agarose/EtBr gels in 1×TBE buffer. As a DNA size marker we used a 1 Kb DNA Ladder. ds cDNA was then precipitated by addition of a half volume of 4M ammonium acetate (about 35 ul) and 3.7 volumes of 95% ethanol (about 260 ul). After vortexing, the tube was immediately centrifuged at 14,000 r.p.m. in a microcentrifuge for 20 min. The pellet was washed with 80% ethanol without vortexing, centrifuged as above for 10 min, air dried, and dissolved in 10 µl of deionized water. Yield of ds cDNA after amplification step was about 5 µg. The ds cDNA was denatured by adding 1 µl of 10× denaturing solution (1 M NaOH, 10 mM EDTA) and incubating at 65° C. for 20 min. All cDNA probes were transferred in 384-well plate and loaded on positively charged nylon membrane (Schleher & Schull) using 384 pin tool and Biomek 2000 (Beckman) robot.

Example 4

Hybridization $^{32}$P-labeled cDNA Target with cDNA ARRAY

A solution of ExpressHyb™ (CLONTECH) and sheared salmon testes DNA (Sigma) was prepared by prewarming 15 ml of ExpressHyb™ at 50–60° C., heating 1.5 mg of sheared salmon testes DNA at 95–100° C. for 5 min followed by chilling quickly on ice, and combining the resultant heat-denatured sheared salmon testes DNA with the prewarmed ExpressHyb™.

A cDNA ARRAY (Atlas™Human cDNA Expression Array, Clontech, Palo Alto, Calif.) was then placed in a hybridization bottle and 10 ml of the solution prepared above was added to the bottle. Prehybridization was performed for 30 min with continuous agitation at 72° C. Labeled cDNA probe (Example 1, about 200 ul, total about 2–5×10$^6$ cpm) with 1/10th of the total volume (about 22 ul) of 10× denaturing solution (1 M NaOH, 10 mM EDTA) was mixed and incubated at 65° C. for 20 min. 5 µl (1 µg/ul) of human Cot-1 DNA was then added, and an equal volume (about 225 µl) of 2×Neutralizing solution (1M NaHPO4, pH 7.0) was added and incubation continued at 65° C. for 10 min. The mixtures were then combined and thoroughly mixed.

The prehybridization solution was then replaced with the solution comprising the labeled oligonucleotide as prepared above and allowed to hybridize overnight with continuous agitation at 65° C. Following hybridization, the hybridization solution was carefully removed and discarded, replaced with 200 ml of Wash Solution 1 (2×SSC, 1% SDS). The ARRAY was washed for 20 min with continuous agitation at 65° C. Washing was repeated four times.

Two additional 20-min washes were then performed in 200 ml of prewarmed Wash Solution 2 (0.1×SSC, 0.5% SDS) with continuous agitation at 65° C. Using forceps, cDNA ARRAY was removed from the container and excess wash solution was removed by shaking.

The damp membrane was immediately wrapped in plastic wrap, mounted on Whatman paper (3 mm Chr). Exposed to x-ray film at −70° C. with an intensifying screen.

Example 5

Comparison Between Using Sets of Gene Specific Primers and Oligo dT

FIG. 1 of application Ser. No. 08/859,008 filed May 21, 1997 (the disclosure of which is herein incorporated by reference) illustrates the effectiveness of using $^{32}$P-labelled polynucleotide target generated using sets of gene specific primers according to the subject invention in hybridization with a cDNA array of 588 probes immobilized on a nylon membrane.

$^{32}$P-labeled cDNA target were synthesized by M-MLV reverse transcriptase from a mixture 588 antisense gene-specific primers (B) or oligo dT(A) using placenta polyA+ RNA as a template as described in Example 1. Primer extension products generated by reverse transcription were purified by gel filtration as described in Example 1 and hybridized separately with two cDNA arrays comprising 588 human genes under identical conditions as described in Example 4. The arrows in pattern B indicate the position of signals which can be detected by using cDNA target generated using the set of gene specific primers but can not be detected by using conventional target generated with oligo dT primers (pattern A). The level of non-specific background detected as signal generated by membrane alone outside of the regions with immobilized probes generated by target generated using oligo dT primers was significantly higher (filter A) in comparison with the background generated by the target generated by using the sets of gene specific primers (filter B).

It is evident from the above results and discussion that the subject invention provides for improved methods of assaying for differential expression. With the subject methods, specificity and efficiency are improved, as compared to previous methods of differential gene expression analysis in which sets of gene specific primers are not employed to generate labeled nucleic acids.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6352829B1). An electronic copy of the "Sequence Listing" will also be available from the USPTO upon request and payment of the fee set forth in 37 CFR 1.19(b)(3).

What is claimed is:

1. A method of producing a sub-population of labeled nucleic acids, said method comprising:

obtaining a sample of nucleic acids from a physiological source; and generating a sub-population of labeled nucleic acids from said sample by contacting said sample with a pool of a representative number of at least 50 distinct gene specific primers under conditions sufficient to enzymatically generate a sub-population of nucleic acids, wherein each constituent distinct gene specific primer of said pool has a nucleotide sequence that is complementary to a distinct mRNA and wherein each labeled nucleic acid is generated using a single gene specific primer.

2. The method according to claim 1, wherein said sample of nucleic acids comprises mRNA.

3. The method according to claim 1, wherein said pool comprises at least 75 distinct gene specific primers.

4. The method according to claim 1, wherein the labeled nucleic acids are first strand cDNA.

5. A method of producing a sub-population of labeled nucleic acids, said method comprising:

obtaining a sample of mRNAs from a physiological source;

contacting said sample with a pool of at least 50 distinct gene specific primers, wherein each constituent distinct gene specific primer of said pool has a nucleotide sequence that is complementary to a distinct mRNA to produce hybrid duplexes between complementary gene specific primers and mRNAs present in said sample; and enzymatically extending said hybrid duplexes to produce said sub-population of labeled nucleic acids wherein each labeled nucleic acid is produced by enzymatic extension which utilizes a single gene specific primer.

6. The method according to claim 5, wherein said pool comprises at least 75 distinct gene specific primers.

7. The method according to claim 5, wherein the labeled nucleic acids are first strand cDNA.

8. A method of analyzing the differences in the RNA profiles between a plurality of different physiological sources, said method comprising:

obtaining a sample of ribonucleic acids or nucleic acid derivatives thereof from each of the distinct physiological sources;

generating a sub-population of labeled nucleic acids for each of the different physiological sources by using a pool of at least 50 distinct gene specific primers, wherein each constituent distinct gene specific primer of said pool has a nucleotide sequence that is complementary to a distinct mRNA and wherein each labeled nucleic acid is generated using a single gene specific primer; and comparing the populations of labeled nucleic acids for each physiological source to identify differences in the populations.

9. The method according to claim 8, wherein the comparing step comprises hybridizing the labeled nucleic acids for each of the distinct physiological sources to an array of probe nucleic acids stably associated with the surface of a substrate to produce a hybridization pattern for each of the different physiological sources; and comparing the hybridization patterns for each of the different physiological sources.

10. The method according to claim 8, wherein the labeled nucleic acids are first strand cDNA.

* * * * *